US009824507B2

United States Patent
Chen

(10) Patent No.: US 9,824,507 B2
(45) Date of Patent: Nov. 21, 2017

(54) MOBILE DEVICE BASED VEHICLE DIAGNOSTIC SYSTEM

(71) Applicant: Innova Electronics, Inc., Irvine, CA (US)

(72) Inventor: Ieon C. Chen, Laguna Hills, CA (US)

(73) Assignee: Innova Electronics Corporation, Irvine, CA (US)

( * ) Notice: Subject to any disclaimer, the term of this patent is extended or adjusted under 35 U.S.C. 154(b) by 0 days.

(21) Appl. No.: 14/509,796

(22) Filed: Oct. 8, 2014

(65) Prior Publication Data

US 2015/0032607 A1  Jan. 29, 2015

Related U.S. Application Data

(63) Continuation-in-part of application No. 13/235,282, filed on Sep. 16, 2011, now Pat. No. 8,880,274, which is a continuation of application No. 11/172,293, filed on Jun. 30, 2005, now Pat. No. 8,024,083.

(51) Int. Cl.

| | |
|---|---|
| *G01M 17/00* | (2006.01) |
| *G06F 7/00* | (2006.01) |
| *G07C 5/00* | (2006.01) |
| *G06Q 20/14* | (2012.01) |
| *G06Q 10/08* | (2012.01) |
| *H04W 4/00* | (2009.01) |
| *G07C 5/08* | (2006.01) |
| *G06F 19/00* | (2011.01) |

(52) U.S. Cl.
CPC ............ *G07C 5/008* (2013.01); *G06F 19/70* (2013.01); *G06Q 10/083* (2013.01); *G06Q 20/145* (2013.01); *G07C 5/085* (2013.01); *H04W 4/008* (2013.01); *G07C 2205/02* (2013.01)

(58) Field of Classification Search
CPC ........................ G06Q 10/20; G06Q 30/0206
USPC .......... 701/2, 24, 29.1, 29.4, 29.7; 455/419, 455/423, 424, 412.2, 414.2
See application file for complete search history.

(56) References Cited

U.S. PATENT DOCUMENTS

| | | | | |
|---|---|---|---|---|
| 2,292,387 A | * | 8/1942 | Markey .................... | H04L 9/38 200/46 |
| 5,347,211 A | | 9/1994 | Jakubowski | |
| 5,400,018 A | * | 3/1995 | Scholl .................... | G07C 5/008 340/10.3 |

(Continued)

FOREIGN PATENT DOCUMENTS

WO    WO 0186576    11/2001

*Primary Examiner* — Khoi Tran
*Assistant Examiner* — Jorge Peche
(74) *Attorney, Agent, or Firm* — Stetina Brunda Garred and Brucker

(57) ABSTRACT

A vehicular diagnostic communications system, and components thereof, are provided for an apparatus and technique for communicating vehicular diagnostic information over a cellphone network. The system includes a code reader having a vehicle diagnostic port connector for receiving vehicle diagnostic information from the vehicle diagnostic port. The code reader also has a local connectivity network circuit for communicating vehicle diagnostic information between the vehicle diagnostic port connector and a local connectivity circuit. A cellphone is arranged in communication with the local connectivity network for communicating vehicle diagnostic information between the code reader and a cellular telephone network.

46 Claims, 7 Drawing Sheets

(56) References Cited

U.S. PATENT DOCUMENTS

| | | | |
|---|---|---|---|
| 5,442,553 A * | 8/1995 | Parrillo | G06F 8/65 455/420 |
| 5,535,274 A * | 7/1996 | Braitberg | H02J 7/0004 379/426 |
| D377,622 S | 1/1997 | Chen | |
| 5,619,412 A * | 4/1997 | Hapka | B60R 25/04 123/179.2 |
| 5,635,841 A | 6/1997 | Taylor | |
| 5,668,880 A * | 9/1997 | Alajajian | H04B 1/707 370/335 |
| 5,732,074 A * | 3/1998 | Spaur | G07C 5/008 370/313 |
| 5,758,300 A | 5/1998 | Abe | |
| 5,767,681 A | 6/1998 | Huang | |
| 5,809,437 A | 9/1998 | Breed | |
| 5,859,628 A | 1/1999 | Ross et al. | |
| 5,884,202 A | 3/1999 | Arjomand | |
| 5,897,605 A * | 4/1999 | Kohli | G01C 21/26 342/457 |
| 5,961,561 A * | 10/1999 | Wakefield, II | G01M 17/007 180/907 |
| 6,000,413 A | 12/1999 | Chen | |
| 6,029,000 A * | 2/2000 | Woolsey | G06F 8/47 717/114 |
| 6,031,497 A * | 2/2000 | Nam | H01Q 1/084 343/702 |
| 6,055,468 A | 4/2000 | Kaman et al. | |
| 6,094,609 A | 7/2000 | Arjomand | |
| 6,122,514 A * | 9/2000 | Spaur | H04W 72/042 370/468 |
| 6,169,943 B1 | 1/2001 | Simon et al. | |
| 6,225,898 B1 | 5/2001 | Kamiya et al. | |
| 6,263,268 B1 * | 7/2001 | Nathanson | G07C 5/008 340/870.01 |
| 6,263,322 B1 * | 7/2001 | Kirkevold | G06Q 30/0283 705/400 |
| 6,389,337 B1 | 5/2002 | Kolls | |
| 6,438,471 B1 | 8/2002 | Katagishi et al. | |
| 6,499,385 B2 | 12/2002 | Protti | |
| 6,535,112 B1 | 3/2003 | Rothshink | |
| 6,587,768 B2 | 7/2003 | Chene et al. | |
| 6,611,740 B2 | 8/2003 | Lowrey et al. | |
| 6,650,318 B1 | 11/2003 | Arnon | |
| 6,718,425 B1 | 4/2004 | Pajakowski et al. | |
| 6,732,031 B1 | 5/2004 | Lightner et al. | |
| 6,807,469 B2 | 10/2004 | Funkhouser et al. | |
| 6,836,708 B2 | 12/2004 | Tripathi | |
| 6,847,916 B1 | 1/2005 | Ying | |
| 6,868,369 B2 | 3/2005 | Huang | |
| 6,925,368 B2 | 8/2005 | Funkhouser et al. | |
| 6,940,270 B2 | 9/2005 | Chen | |
| D510,287 S | 10/2005 | Chen | |
| 6,957,133 B1 | 10/2005 | Hunt et al. | |
| 6,959,187 B2 * | 10/2005 | Grossi | G07F 9/026 455/423 |
| 6,968,733 B2 | 11/2005 | Andreasen | |
| 7,030,742 B2 | 4/2006 | Treadway | |
| 7,085,680 B2 | 8/2006 | Huang | |
| 7,116,216 B2 | 10/2006 | Andreasen | |
| D334,560 S | 4/2007 | Wilson | |
| 7,209,813 B2 | 4/2007 | Namaky | |
| RE39,619 E | 5/2007 | Andreasen | |
| D545,223 S | 6/2007 | Chen | |
| D559,137 S | 1/2008 | Protti | |
| D560,129 S | 1/2008 | Rich | |
| D560,527 S | 1/2008 | Rich | |
| D588,621 S | 1/2008 | Rich | |
| 7,325,775 B2 | 2/2008 | Chen | |
| D563,249 S | 3/2008 | Chen | |
| 7,363,149 B2 | 4/2008 | Klausner et al. | |
| D569,280 S | 5/2008 | Chen | |
| 7,376,497 B2 | 5/2008 | Chen | |
| D571,241 S | 6/2008 | Andreasen | |
| 7,437,227 B2 | 10/2008 | Andreasen | |
| D581,822 S | 12/2008 | Madison | |
| 7,464,000 B2 | 12/2008 | Huang | |
| D590,387 S | 4/2009 | Chen | |
| 7,520,668 B2 | 4/2009 | Chen | |
| RE40,798 E | 6/2009 | Chen | |
| RE40,799 E | 6/2009 | Chen | |
| 7,603,293 B2 | 10/2009 | Chen | |
| 7,620,484 B1 * | 11/2009 | Chen | G06Q 20/102 701/31.5 |
| D610,586 S | 2/2010 | Chen | |
| 7,734,390 B2 | 6/2010 | Chen | |
| 7,778,750 B2 | 8/2010 | Knight et al. | |
| D624,446 S | 9/2010 | Chen | |
| D624,838 S | 10/2010 | Chen | |
| D625,209 S | 10/2010 | Chen | |
| D625,210 S | 10/2010 | Chen | |
| D625,634 S | 10/2010 | Chen | |
| 7,904,219 B1 | 3/2011 | Lowrey et al. | |
| 7,974,750 B2 | 7/2011 | Namaky | |
| 8,019,503 B2 | 9/2011 | Andreasen | |
| 8,024,083 B2 | 9/2011 | Chen | |
| D646,188 S | 10/2011 | Chen | |
| D646,599 S | 10/2011 | Chen | |
| 8,032,419 B2 | 10/2011 | Chen | |
| 8,068,951 B2 | 11/2011 | Chen et al. | |
| 8,301,329 B2 | 10/2012 | Andreasen | |
| 8,306,687 B2 | 11/2012 | Chen | |
| 8,370,018 B2 | 2/2013 | Andreasen et al. | |
| 8,509,986 B1 | 8/2013 | Chen | |
| 8,630,765 B2 | 1/2014 | Chen | |
| 8,825,271 B2 | 9/2014 | Chen | |
| 8,831,814 B2 | 9/2014 | Chen | |
| 8,855,621 B2 | 10/2014 | Chen | |
| 8,862,117 B2 | 10/2014 | Chen | |
| 8,880,274 B2 | 11/2014 | Chen | |
| 8,909,416 B2 | 12/2014 | Chen et al. | |
| 9,019,092 B1 * | 4/2015 | Brandmaier | B60R 25/102 340/426.1 |
| 2003/0078039 A1 * | 4/2003 | Grossi | G07F 9/026 455/423 |
| 2003/0138475 A1 * | 7/2003 | Chen | C05F 11/08 424/435 |
| 2003/0171111 A1 | 9/2003 | Clark | |
| 2004/0110472 A1 | 6/2004 | Witkowski | |
| 2004/0153884 A1 * | 8/2004 | Fields | H04L 1/22 714/52 |
| 2004/0203379 A1 * | 10/2004 | Witkowski | H04L 12/66 455/41.2 |
| 2005/0125115 A1 * | 6/2005 | Hiwatashi | G01C 21/26 701/25 |
| 2005/0282539 A1 * | 12/2005 | Grossi | G07F 9/026 455/423 |
| 2006/0101311 A1 * | 5/2006 | Lipscomb | G07C 5/008 714/47.1 |
| 2007/0073459 A1 * | 3/2007 | Webster | G07C 5/0816 701/31.4 |
| 2007/0233341 A1 * | 10/2007 | Logsdon | G07C 5/008 701/31.5 |
| 2007/0250228 A1 * | 10/2007 | Reddy | B60R 25/00 701/31.4 |
| 2008/0015748 A1 * | 1/2008 | Nagy | G07C 5/008 701/31.4 |
| 2009/0276115 A1 * | 11/2009 | Chen | G07C 5/008 701/29.6 |
| 2011/0224866 A1 * | 9/2011 | Chen | G07C 5/0808 701/31.4 |
| 2011/0264322 A1 | 10/2011 | Chen | |
| 2012/0215398 A1 | 8/2012 | Chen | |
| 2013/0304278 A1 * | 11/2013 | Chen | G06F 17/00 701/2 |
| 2014/0032038 A1 * | 1/2014 | Namaky | H04L 67/125 701/29.4 |
| 2014/0046800 A1 | 2/2014 | Chen | |
| 2014/0052328 A1 | 2/2014 | Nguyen | |
| 2014/0052531 A1 * | 2/2014 | Kent | G06Q 30/02 705/14.49 |

(56) References Cited

U.S. PATENT DOCUMENTS

| | | | |
|---|---|---|---|
| 2014/0195099 A1* | 7/2014 | Chen | G07C 5/0808 701/29.6 |
| 2014/0195101 A1* | 7/2014 | Chen | G07C 5/008 701/29.6 |
| 2015/0066781 A1* | 3/2015 | Johnson | G06Q 30/0206 705/305 |
| 2015/0187146 A1* | 7/2015 | Chen | G07C 5/008 701/31.5 |
| 2015/0206357 A1* | 7/2015 | Chen | G07C 5/008 701/31.4 |
| 2015/0226563 A1* | 8/2015 | Cox | G07C 5/00 701/29.1 |
| 2015/0228129 A1* | 8/2015 | Cox | G07C 5/0808 701/29.1 |
| 2016/0078403 A1* | 3/2016 | Sethi | G06Q 10/0875 705/26.81 |

\* cited by examiner

MOBILE DEVICE BASED VEHICLE DIAGNOSTIC SYSTEM

CROSS-REFERENCE TO RELATED APPLICATIONS

This application is a continuation-in-part of U.S. patent application Ser. No. 13/235,282, filed Sep. 16, 2011, which is a continuation of U.S. patent application Ser. No. 11/172,293, filed on Jun. 30, 2005, now U.S. Pat. No. 8,024,083, the contents of which are expressly incorporated herein by reference.

STATEMENT RE: FEDERALLY SPONSORED RESEARCH/DEVELOPMENT

Not Applicable

BACKGROUND

The present invention relates to automotive communication systems and, more particularly, to communication systems for interfacing automotive diagnostic systems and remote diagnostic, repair and emergency services.

Vehicle diagnostic systems have evolved in many ways to provide detailed information regarding the status of multiple vehicle systems. Such diagnostic systems may also be queried to output different information, as well as be programmed to modify vehicle operational parameters. As the sophistication of vehicle diagnostic systems grows, however, the requirements for supporting equipment can become more specialized, and the operational complexity of the supporting equipment may be beyond the level of ordinary consumers.

The increasing sophistication of vehicle diagnostic systems has also given rise to a variety of communication systems for interfacing the vehicle diagnostic system to wireless networks, for routing vehicle owners to service providers, the internet and elsewhere. Business models for various automatic systems have emerged, based on different commercial approaches for interfacing communication networks to vehicle voice and data systems.

One such contemporary business model is exemplified by the OnStar™ system, operated by General Motors Corporation. The system typically includes a wireless appliance installed in the vehicle, wired to the vehicle diagnostic system. The wireless appliance may include, or be wired to a global position satellite (GPS) system, for generating information respecting the location of the vehicle. OnStar™ system also allows remote operation of certain vehicle systems, e.g. unlocking the doors. The OnStar™ service is typically provided on a subscription basis, with the first year being free of charge with the purchase of qualifying vehicles, i.e. typically higher priced vehicles.

Another wireless vehicle system of note is the LoJack™ system for protecting vehicle theft conditions, and monitoring the location of the vehicle in the event that it is stolen or lost. Like the OnStar™ system, the LoJack™ system utilizes a wireless appliance that incorporates a GPS system, communicates to a dedicated receiver, and charges a subscription fee to maintain and support the data link.

While dedicated communication links such as those utilized in the OnStar™ system and the LoJack™ system, can provide useful diagnostic services and security in relation to a variety of circumstances, such systems suffer from a variety of practical and economic factors that tend to limit their use and customer base.

A common shortcoming of such contemporary systems is that they typically require dedicated hardware, e.g. a wireless appliance mounted to a vehicle, and electrically connected to the vehicle computer. Such hardware is typically installed by a trained installer or by original car manufacturer. Moreover, the hardware relies upon a dedicated wireless communication link to a specific service provider. Consequently, the user may feel captive to a particular diagnostic subscription service. Such systems may be viewed as expensive, of limited functionality, and tend to be standard equipment only in higher priced vehicles.

Given the rapid evolution of cellphones, and the proliferation of multiservice cellular telephone networks, the need for accessing a diagnostic system communications link may be better served by cellphones, and which allow a broader choice of contacts. In relation to conventional prior art systems, it would be desirable to provide a diagnostic communication system that does not require mounting to a vehicle chassis, or need installation by a trained installer. It is desirable to provide a diagnostic communication system that does not require a dedicated communications link, but rather allows a user to connect to a variety of generally available contacts on the cellular network, public telephone network and the internet, without the need for participation in a subscription communication service. It is further desirable to provide a diagnostic communication system that is installable, removable, hand transportable and plug connectable to different vehicles, without the need for trained assistance or service registration. It is desirable to provide a hand transportable diagnostic communication system, that allows for internal storage of vehicle diagnostic information, and transfer of the information, wirelessly and/or manually, to a general purpose computer. Such manual data transport would allow for storage and communication of data to a remote service provider, even when communication via cellular telephone network or local connectivity circuit is unavailable. As described below, the present invention, in different combination embodiments, addresses these and other improvements to contemporary vehicle diagnostic communication systems, and business methods related thereto.

BRIEF SUMMARY

A vehicular diagnostic communications system, and components thereof, are provided for an apparatus and technique for communicating vehicular diagnostic information over a cellphone network. The system includes a code reader having a vehicle diagnostic port connector for receiving vehicle diagnostic information from the vehicle diagnostic port. The code reader also has a local connectivity network circuit for communicating vehicle diagnostic information between the vehicle diagnostic port connector and a local connectivity circuit. A cellphone is arranged in communication with the local connectivity network for communicating vehicle diagnostic information between the code reader and a cellular telephone network.

The cellphone functionality in the present invention may be alternately implemented using a personal data assistant or similar devices for interfacing a local connectivity network and a cellular network.

The local connectivity network may be implemented in a variety of forms, such as the 802.11 format, Bluetooth™, etc. Alternatively, the local connectivity network may be implemented as an infrared communications network, operating in accordance with generally utilized communications protocols for such systems. Such communication of diagnostic information and control signals via the cellphone provides choice of service provider or other contact to which the data is to be communicated. It also allows for voice communication in conjunction with data transfer and evaluation.

A variety of functions may be implemented on the cellphone and/or code reader to initiate a diagnostic communications link, or to indicate receipt of an interrogation signal, representing initiation of diagnostic activity or receipt of diagnostic data.

The cellphone and/or code reader may also be equipped with a GPS locator circuit to provide location information that may be communicated within the communication link to facilitate various functions that may be implemented within the scope of the present invention, e.g. location of nearest automotive parts store/service provider/etc.

A code reader construction in accordance with the present invention may be implemented utilizing conventional code reader, modified with an adapter that links the code reader to a local connectivity network. That implementation permits considerable efficiency, and readily allows conventional use of a code reader where access to a local connectivity circuit is not available. Where the code reader is adapted pursuant to the present invention, or where provided with a local connectivity circuit, the invention provides a computer data port connector that allows for direct connection of the code reader to a personal computer data port, such as a USB port. In some implementations the code reader may be engagable to and supportable by connection to the vehicle diagnostic port and/or the computer data port.

According to another aspect of the invention, there is provided a diagnostic system for diagnosing a vehicle associated with vehicle identification information. The diagnostic system includes a diagnostic device having a vehicle diagnostic port connector for receiving vehicle diagnostic data from a vehicle diagnostic port located on the vehicle, and a local wireless communication circuit, in communication with the vehicle diagnostic port, for communicating vehicle diagnostic data between the vehicle diagnostic port connector and a local wireless communication network. An intermediate wireless communication device is in communication with the local wireless communication network for receiving vehicle diagnostic data from the diagnostic device. The diagnostic system further includes a diagnostic database in wireless communication with the intermediate wireless communication device, wherein the diagnostic database is configured to match the diagnostic data from the vehicle with a most likely solution associated with a repair part. A repair parts database is in communication with the diagnostic database and is configured to match the repair part with a universal part identification number based in part on the vehicle identification information associated with the vehicle.

The universal part identification number may be an Aftermarket Catalog Enhanced Standard (ACES) part number.

The diagnostic device may be adapted to receive the vehicle identification information from the vehicle through the vehicle diagnostic port connector. The diagnostic device may automatically upload diagnostic data to the intermediate wireless communication device when the diagnostic device moves into an area associated with the intermediate wireless communication device. The area associated with the intermediate wireless communication device may be of a radius equal to 10-100 yards.

The diagnostic system may additionally include an inventory database in communication with the repair parts database, wherein the inventory database is configured to search for an inventoried part associated with the universal part identification number. A purchasing module may be in communication with the inventory database and configured to conduct a transaction for the purchase of the inventoried part associated with the universal parts identification number.

The intermediate wireless communication device may be a cellphone or a wireless router.

According to another embodiment, there is provided a method of diagnosing a vehicle having vehicle identification information. The method comprises the steps of: retrieving vehicle diagnostic data from the vehicle using a diagnostic device; communicating the vehicle diagnostic data from the diagnostic device to a remote diagnostic database using wireless communication therebetween; analyzing the vehicle diagnostic data at the diagnostic database to match the diagnostic data from the vehicle with a most likely solution associated with a repair part; and matching the repair part with a universal part identification number based in part on the vehicle identification information associated with the vehicle.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
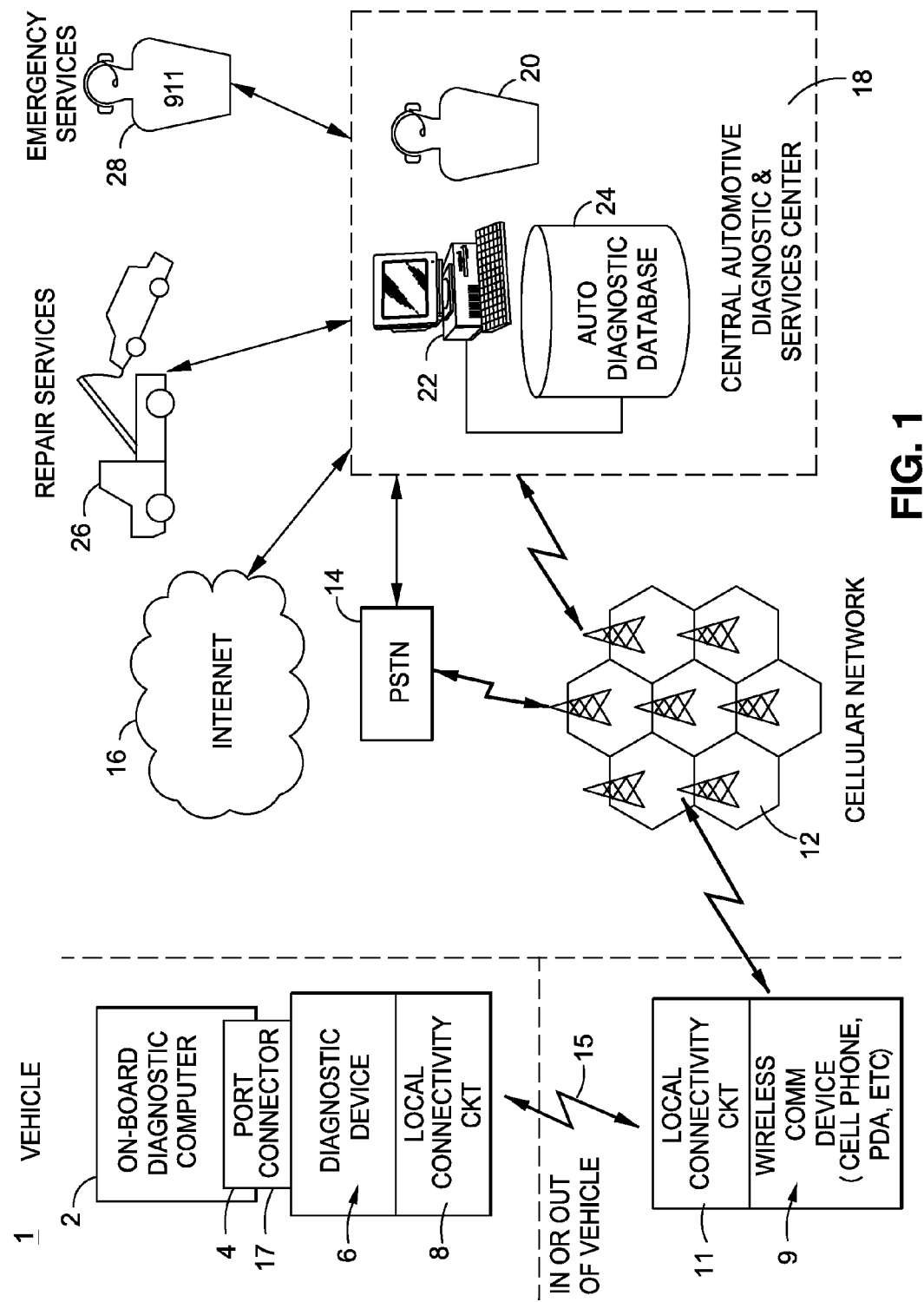
FIG. 1 is a block diagram showing basic functional feature of one embodiment of the invention.

As described more fully below, the present invention utilizes the evolving capacity of cellular telephones to support voice and data information, to avoid the need for installing dedicated wireless devices to communicate between the diagnostic system and a cellular network, or other dedicated radio frequency systems. Such contemporary cellphones incorporate a user visual interface, a series of input keys, an internal processor, internal storage, and communications links adapted for bidirectional communication of voice, data and control signals, sufficient to access and communicate diagnostic information and related control signals.

In one embodiment of the invention diagnostic information and/or control signals are communicated between the cellphone network and the vehicle on-board computer via a radio frequency local connectivity network, such as a Bluetooth™, Wi-Fi network, or an infrared network. The link between the local connectivity network and the vehicle computer may be implemented using a code reader or scan tool (collectively referred to as a "code reader"), modified to incorporate local connectivity communication circuit. The link between the local connectivity network and the cellular network may be implemented using a cellphone/smartphone or personal data assistant incorporating a Bluetooth™, Wi-Fi or infrared connectivity circuit. As such, the code reader may operate to perform conventional functions of accessing and downloading vehicle diagnostic information, which may then be communicated to the cellular network via the scan tool/cellphone local connectivity network.

Where the code reader is not engaged in communication with a local connectivity network (e.g. not located proximate a Bluetooth™ enabled cellphone), the code reader can store the diagnostic information for review or be used to manually transport data from the vehicle to be uploaded from to a remote personal computer, (e.g. by USB connector or personal computer supported local connectivity network), for communication with a remote service provider. The code reader local connectivity circuit may, therefore, be in communication with a personal computer local connectivity circuit. As such, diagnostic information may alternately be communicated from the code reader to a personal computer, for further communication to remote service providers, without use of the cellular network.

In some embodiments the code reader may communicate with other devices, such as a personal data assistant, tablet computer, smartphone, or Blackberry™, (collectively a "personal data assistant") adapted for communication with a local connectivity circuit and/or the cellular telephone network. In further embodiments, the code reader may itself incorporate a cellular network connectivity circuit, for communicating directly between the code reader and the cellular telephone network.

In further embodiments the cellphone and/or code reader may incorporate GPS circuitry to provide location information that may be communicated to a remote service provider along with diagnostic information, via the cellular telephone network and/or manual transport and uploading to a personal computer.

In another implementation, a code reader adapter is provided for interfacing a conventional code reader to a local connectivity network for communicating information accessed by the code reader to a cellphone or personal computer.

Turning now to the drawings, FIG. 1 illustrates basic structure and function of one implementation of the present invention. In the implementation shown therein, vehicle 1 incorporates an onboard diagnostic computer 2, having a vehicle diagnostic port 4. Diagnostic device 6, such as a code reader, has a diagnostic port connector 17 plug, engagable to diagnostic port 4, to access diagnostic information from the vehicle onboard diagnostic computer 2. In other embodiments, connecting cable 19 (see FIG. 3) is provided to connect the diagnostic device 6 to the vehicle onboard computer 2. It is understood that in its simplest form, the diagnostic device 6 merely retrieves data from the vehicle and uploads/transfers the retrieved data to a remote location (e.g., to a mobile communication device, computer, etc.). In this respect, all diagnostic processing may be remote from the diagnostic device 6.

The diagnostic device 6 may be provided with a local connectivity circuit 8, to facilitate communication of diagnostic information and control signals between the diagnostic device 6 and a local connectivity network 15, for communication between the diagnostic device 6 and wireless communication device 9. The wireless communication device 9 may be implemented as a cellphone (which encompasses smartphones, including iPhones™), PDA, Blackberry, tablet computer or other similar mobile devices. The wireless communication device 9 also incorporates a local connectivity circuit 11, which allows local communication between the diagnostic device 6 and the wireless communication device 9. As indicated above, the local connectivity circuit may be implemented using Bluetooth™, Wi-Fi, infrared or other local connectivity networks utilizing signal protocols commonly used for such network.

The wireless communication device 9 is, in turn, in communication with a cellular telephone network 12. The cellular telephone network 12 is, in turn, in communication with Public Switched Telephone Network (PSTN) 14 and/or the Central Automotive Diagnostic and Services Center 18.

According to one embodiment, the central automotive diagnostic and services center 18 includes a computer terminal 22 and interconnected automotive diagnostic database 24. The operator or human interface 20, may thereby receive information from the wireless communication device 10, such as diagnostic trouble codes, which can be correlated into the corresponding diagnostic condition, using automotive diagnostic database 24. The operator or human interface 20 may take steps appropriate to the diagnostic condition, by communicating with repair services 26, emergency services 28, or to other parts or services providers, via internet 16, or by communicating with the user, via the cellular network.

Figure 2:
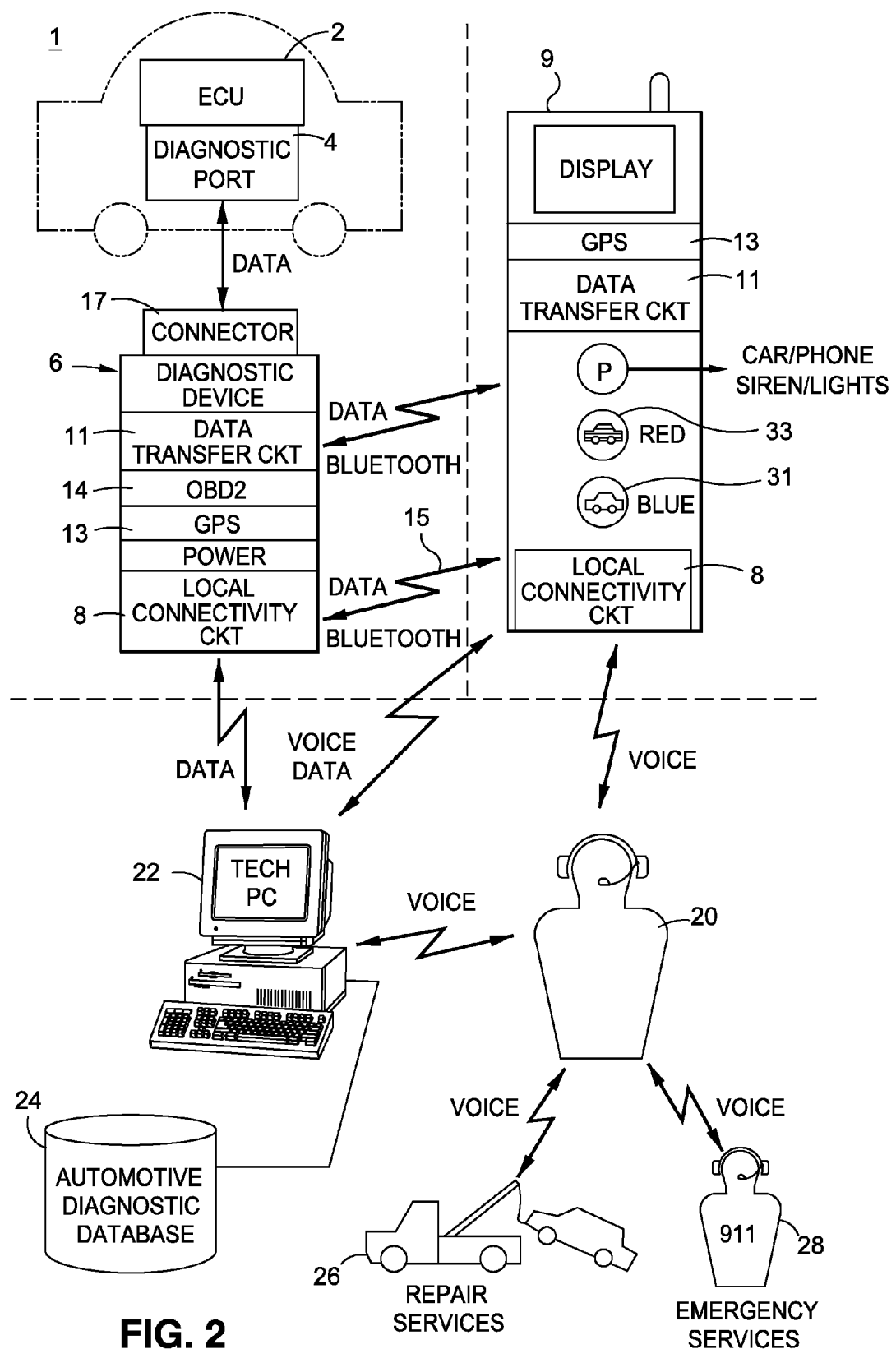
FIG. 2 is a basic block diagram further illustrating functions of additional implementations of the invention.
Figure 3:
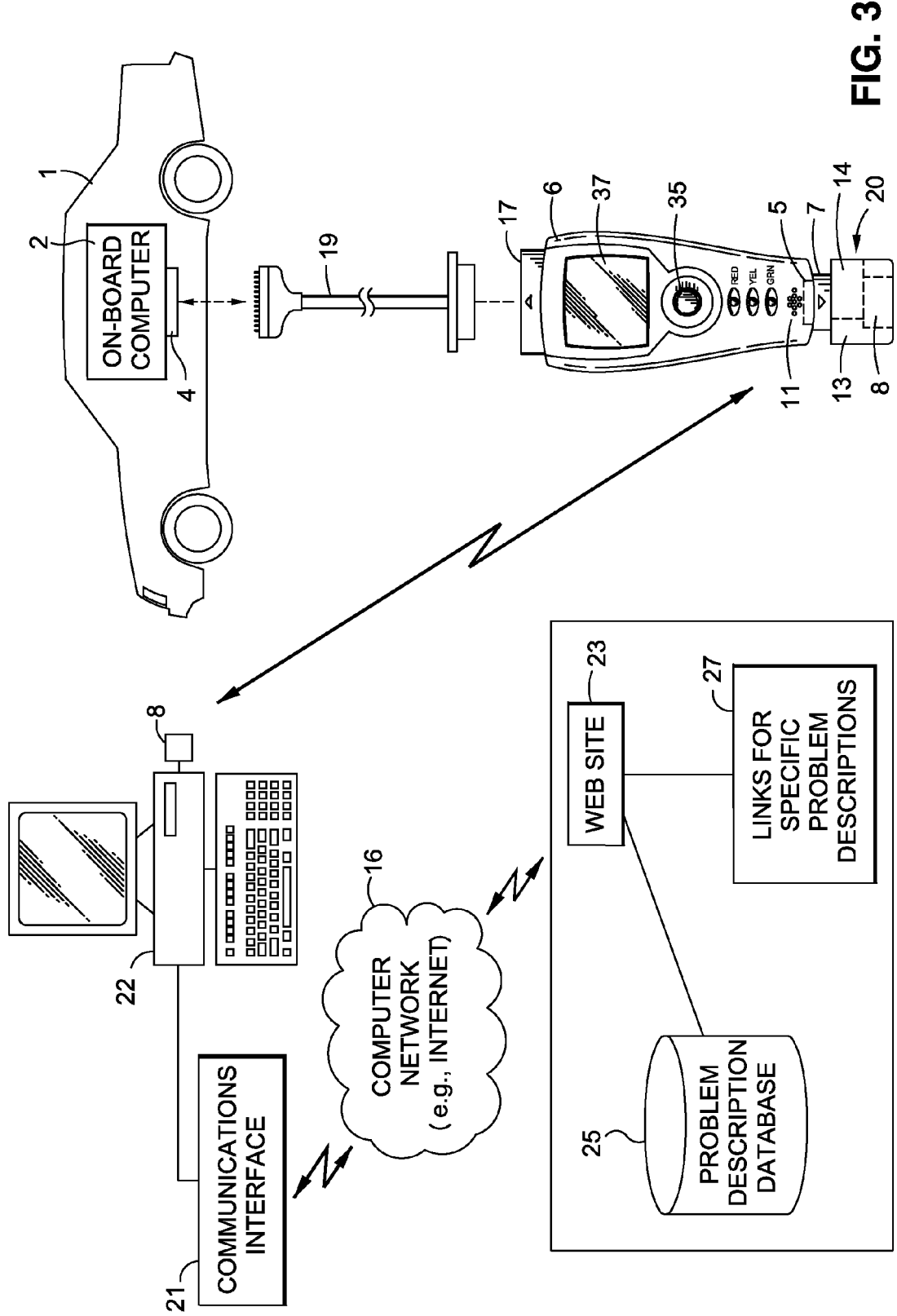
FIG. 3 is a block diagram illustrating additional embodiments of the invention.

FIG. 2 illustrates additional functionality of the present invention in connection with the illustrated embodiment. As shown therein, vehicle 1 again incorporates an onboard diagnostic computer 2 and diagnostic port 4. The diagnostic device 6, sometime referred to as a code reader or scan tool, is in direct electrical connection with the diagnostic port 4, and may be supported thereby. In alternate embodiments the tool 6 may be connected to port 4 via cable 19, as shown at FIG. 3.

When the present invention is implemented using a conventional scan tool or code reader, an adapter is provided to provide connectivity to communicate with the local connectivity network. As shown in FIG. 3, adapter 20 is engaged to device 6, such as by connector 7 engaged to device port 5. Port 5 may be implemented as a USB connector port plug engagable to the adapter 20, or to a USB port of a personal computer.

Adapter 20 includes a local connectivity circuit 8, for data communication with the wireless communication device 9 and/or the computer terminal 22. The adapter 20 may further include a GPS circuit 13 and an OBD II protocol circuit 14.

Most commonly the wireless device 9 may be implemented as a generally conventional cellphone, with functionality for communicating with the diagnostic device 6 or adapter 20, where the adapter is implemented separate from the diagnostic device 6.

Wireless device 9 may incorporate a local connectivity circuit 11, for communicating with the diagnostic device local connectivity circuit 8. The cellphone 9 therefore can communicate data, such as diagnostic information and control signals between the diagnostic device 6 and the cellular telephone network. As such, the onboard computer 2 may be queried, or operating parameters adjusted, as appropriate to access diagnostic information, or change operating conditions within the vehicle.

In one embodiment of the invention as shown in FIG. 2, the cellphone 9, is provided with dedicated function lights, and associated function circuitry, to facilitate communication of diagnostic information. Blue indicator 31 is operative to provide a data ready signal to indicate receipt of diagnostic trouble codes from the diagnostic device local connectivity circuit 8. The blue indicator 31 may also function to initiate a communications link, using the cellular communication network, to communicate with the Central Automotive Diagnostic and Services Center 18 (FIG. 1) or such other telephone number as may be desired by the user.

In one embodiment of the invention pressing the blue indicator 31 may automatically link the cellphone to a preset telephone number. In another embodiment of the invention, depression of the blue button will generate options on the cellphone display, which may be selected by use of the cellphone keyboard. One such option may include manual entry of desired telephone number on the keypad.

Illumination of the red indicator 33 may serve to indicate presence of one or more predetermined trouble codes, or other diagnostic information indicative of a more immediate need for attention. Again, in different embodiments of the invention the red indicator 33 may function as an input button, which may be depressed to initiate a communications link with diagnostic device, e.g. generate an interrogation signal for communication to the diagnostic device 6.

As shown in FIG. 2, the cellphone 9 may further include a GPS circuit 13, as is included in some contemporary cellphones. The GPS information may be encoded and communicated from the cellphone 9 to a remote service provider. Alternatively, as described above, GPS circuitry 13 may be included within diagnostic device 6.

The diagnostic device 6 may be implemented in a variety of forms, including a variety of functions and displays. In the embodiment shown at FIG. 3, the diagnostic device 6 incorporates a connect button 35, operative to electrically connect the diagnostic device 6 to the vehicle onboard computer in response to pressing connect button 35. As such, the diagnostic device may be in operative connection with the onboard computer without the need for user to navigate a user visual interface.

Diagnostic device 6 may also be provided with a display 37 to allow the user to read trouble codes, trouble code descriptors and/or other text or graphic information as may be provided from the vehicle onboard computer, or processed by the diagnostic device 6.

Diagnostic device 6 may further include a plurality of different colored indicators, to indicate the presence of the receipt of diagnostic trouble codes from the onboard computer (red), the absence of trouble codes received from the onboard computer (green), or an incomplete or interrupted test (yellow). The device 6 may further provided with an audio output 11, which may provide an audio signal responsive to functions of the diagnostic device 6.

The diagnostic device 6 may also be provided with an output connector 5, which may be a USB output port that is engageable to connector 7 of local connectivity adapter 20. Diagnostic information from the onboard computer 2 may therefore be communicated to the diagnostic device 6, and thereafter communicated to a local connectivity circuit for communication to a wireless device 8 or computer terminal 22. Alternatively, the diagnostic device 6 connector port 5 may be directly connected to computer terminal 22, e.g. though a USB port, to allow downloading of diagnostic information received from the vehicle onboard computer 2 and stored in the diagnostic device 6. The computer terminal 22 may in turn be connected to the computer network 16, via communications interface 21. The computer network 16 allows the computer terminal 22 to be connected to website 23 which may be linked to a problem description database 25 and/or links for specific problem descriptions 27.

In practice, the diagnostic device 6 may thereby allow either real time or delayed communication of diagnostic information from the vehicle onboard computer 2 to one or more remote locations, wherein vehicle diagnostic information may be analyzed and corrective actions identified. Information respecting parts and services useful for such corrective actions may be communicated to the user and displayed on the diagnostic display 37 or cellphone display. Selection of various functions may be implemented using input buttons on the diagnostic device 6 or cellphone, e.g. keypad, as may be appropriate for different diagnostic conditions.

Figure 4:
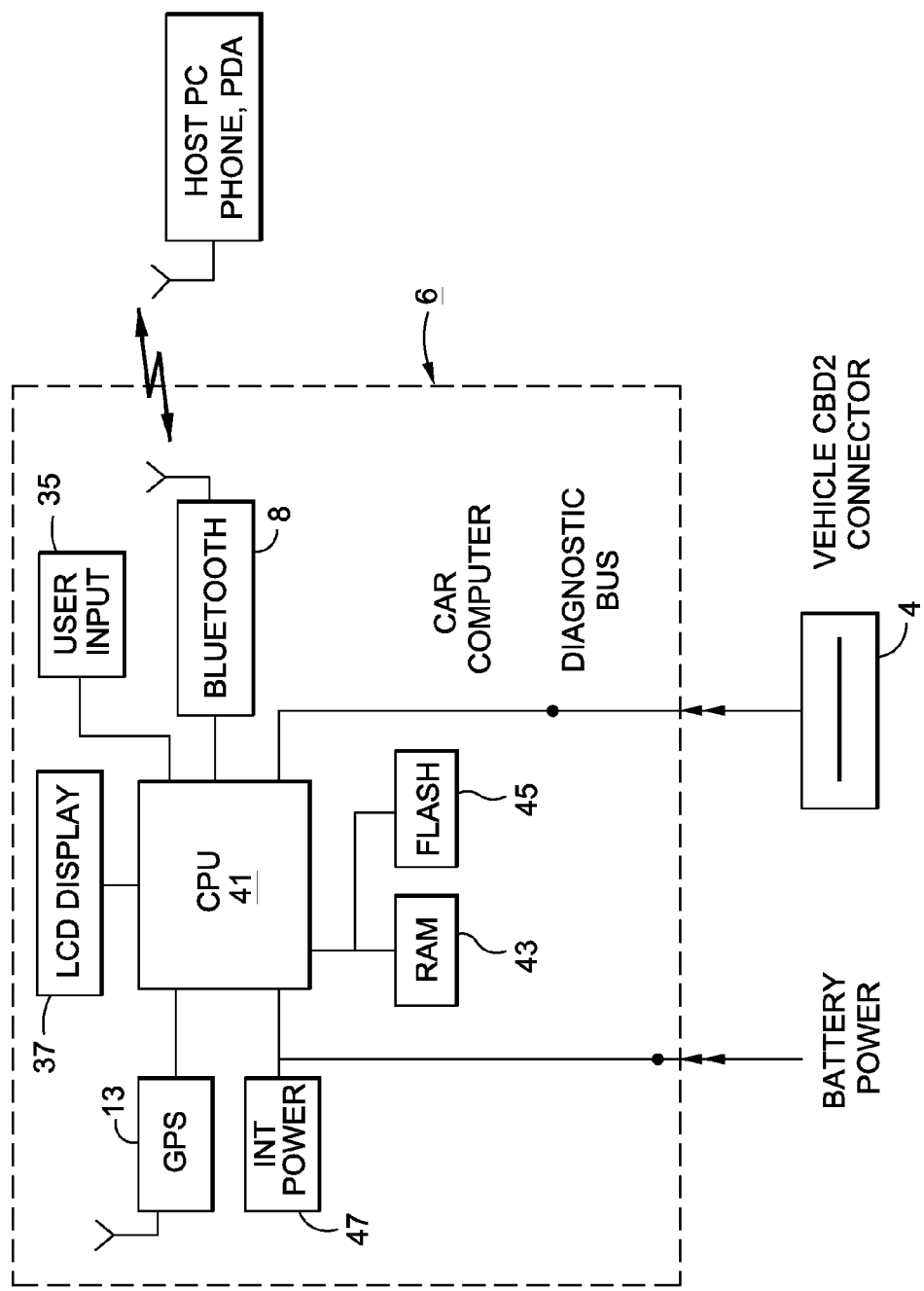
FIG. 4 is a block diagram of a scan tool constructed in accordance with one implementation of the invention.

FIG. 4 illustrates a basic functional diagram of representative of the operation of device 6, in one implementation. As shown therein, the device 6 is adapted for bidirectional communication with a vehicle diagnostic port, a local connectivity circuit, and a USB connector (or the like) for a host PC. As shown therein, the device 6 may include a GPS circuit 13, user inputs 35, (such as keypads or connect buttons) and one or more LCD displays 37. The device 6 may include a central processing unit 41 (CPU) operatively connected to a random access memory 43 (RAM) and a flash memory 45, which may store information such as descriptors associated with particular diagnostic trouble codes received from a vehicle onboard computer. Information stored in the flash memory 45 may be modified in response to data or control signals received through the local connectivity circuit 8 or a USB connector. In one implementation data or control signals from the local connectivity circuit or the USB connector may be communicated to the vehicle onboard computer, in order to perform functions such as obtaining additional vehicle data or modifying settings in the vehicle onboard computer in response to sensed diagnostic information. The device 6 may operate using internal power source 47, or be connected to an external power source.

Figure 5:
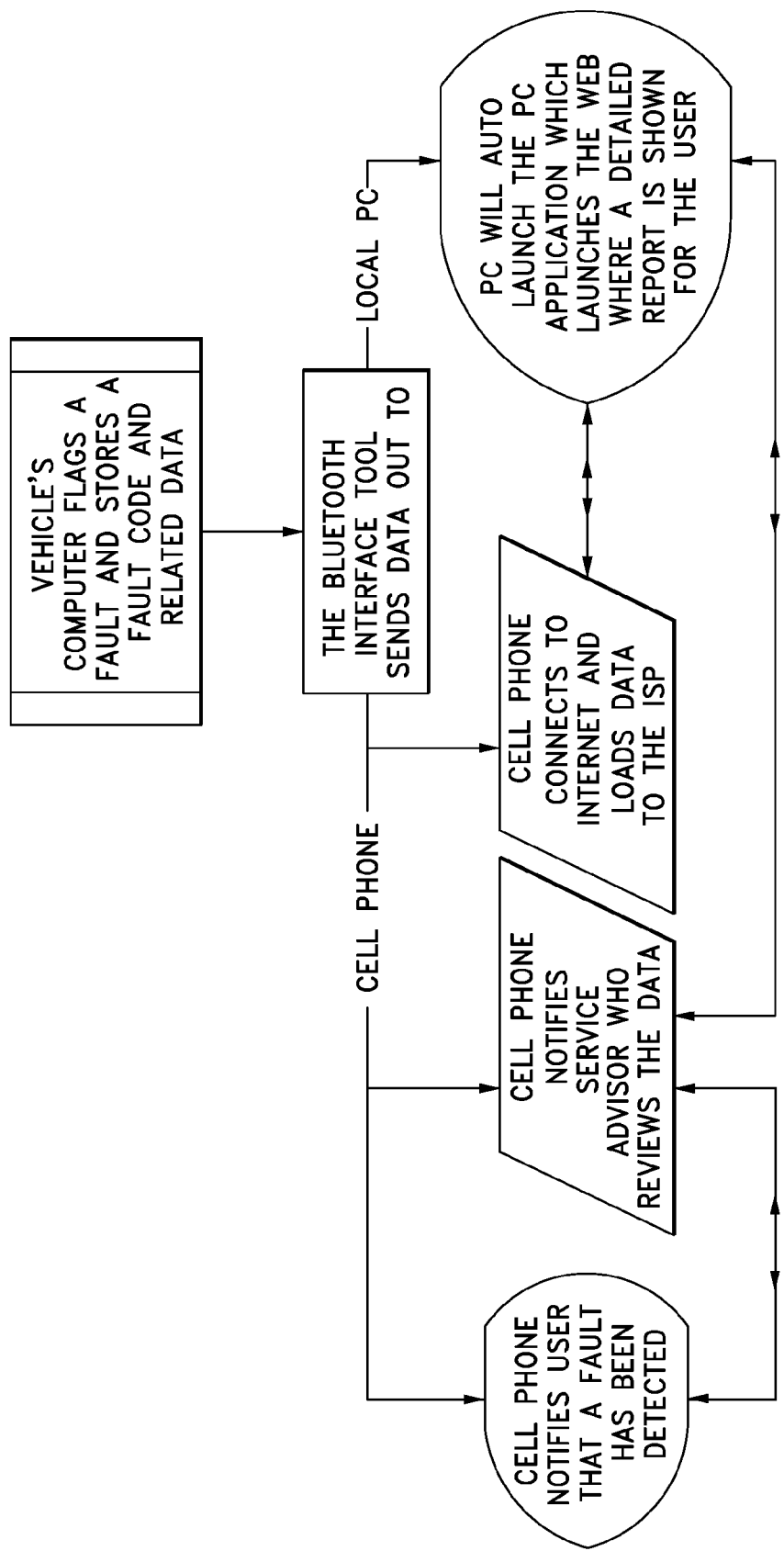
FIG. 5 is a flow chart illustrating the sequence of functions in accordance with one implementation of the invention.

FIG. 5 is a flow chart representing certain operations that may be effected in accordance with one implementation of the present invention. As the process shown therein is initiated when the vehicle flags a fault, and stores a fault code and related vehicle diagnostic data. That information is communicated to a diagnostic device, having a local connectivity circuit formed therein, or formed in an adapter connected to the scan tool. As indicated above, the scan tool may generate visual or audible signals indicating the receipt of the fault codes, and display associated descriptors. The local connectivity circuit can communicate the fault code and related data to nearby equipment having compatible local connectivity circuits, such as Bluetooth equipped cellphone or local computer terminal. Where the fault codes and related data are received by the cellphone, the cellphone may provide the user with information that a fault has been detected, such as by illuminating a dedicated indicator on the cellphone, or by generating an audible signal, or by providing text data on the cellphone display. The cellphone may further proceed to notify a service adviser that fault codes and related data have been received. Such notification may proceed autonomously by programming within the cellphone, or may require the cellphone user to initiate a communication with the service advisor, either by depressing a dedicated button, navigating a cellphone user visual interface, or by entering a desired telephone number.

The cellphone may communicate data, over the cellular telephone network, to a service advisor either by direct cellphone link, by connection to a landline via public switched telephone network, or by connection to internet portal, whereby data is communicated via the internet to an internet service provider.

Where the diagnostic device local connectivity circuit is in communication with a local personal computer, the personal computer may implement connectivity with internet service providers, landline telephones or other systems to provide analysis of the fault codes and related data, as well as any data control signals necessary to obtain additional information from the vehicle onboard computer, or to adjust the operation thereof. Voice communication may also be implemented between the service provider receiving the fault codes and related data, and the user's cellphone, to provide additional information, such as the location of a nearby service facility, emergency service communications, towing services, etc.

Figure 6:
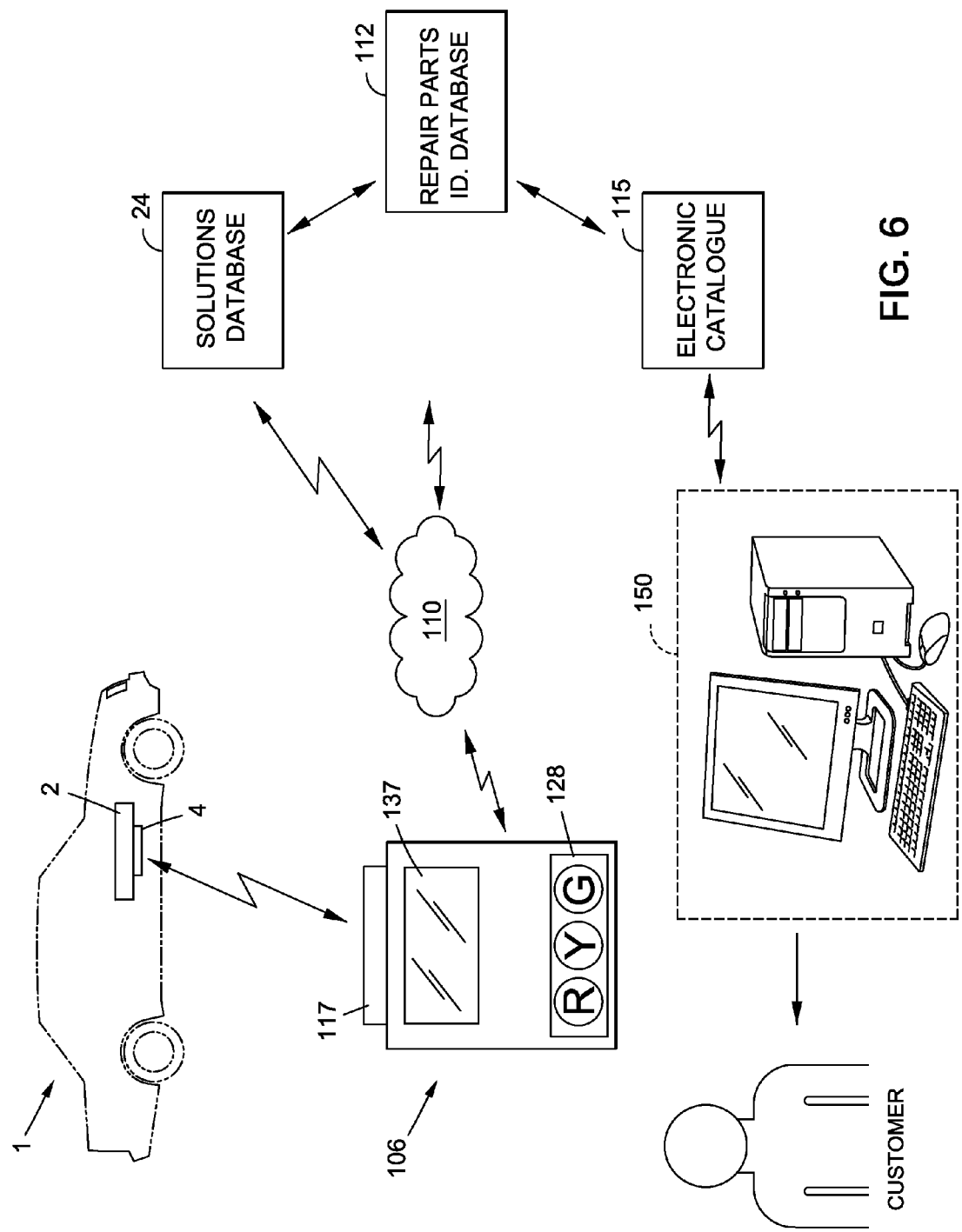
FIG. 6 is a schematic view illustrating an e-commerce system constructed in accordance with an aspect of the present invention.

The foregoing discussion primarily relates to communication of information between the vehicle and a remote location, such as a diagnostic database, wherein an intermediate communication device is used to effectuate communication between a diagnostic device 6 and the remote location. As explained above, the intermediate communication device may be a cellphone, smartphone, tablet computer, PDA, or the like. Furthermore, the foregoing describes various embodiments of diagnostic devices 6, which may be used, including code readers and scan tools. It is also contemplated that the diagnostic device 6 may also take the form of a dongle 106 (see FIG. 6) that is plug connectable to the diagnostic port 4 on the vehicle 1. The dongle 106 may have a relatively small form factor, and may have a very limited or non-existent user interface. Along these lines, one embodiment of the dongle 106 may simply include a small display screen 137 and LED(s) 128 (i.e., red, yellow and/or green) to provide a quick alert to the user of the health of the vehicle 1 based on diagnostic data received therefrom, while other embodiments of the dongle 106 may be formed without any LED(s) 128, or other display resources.

Figure 7:
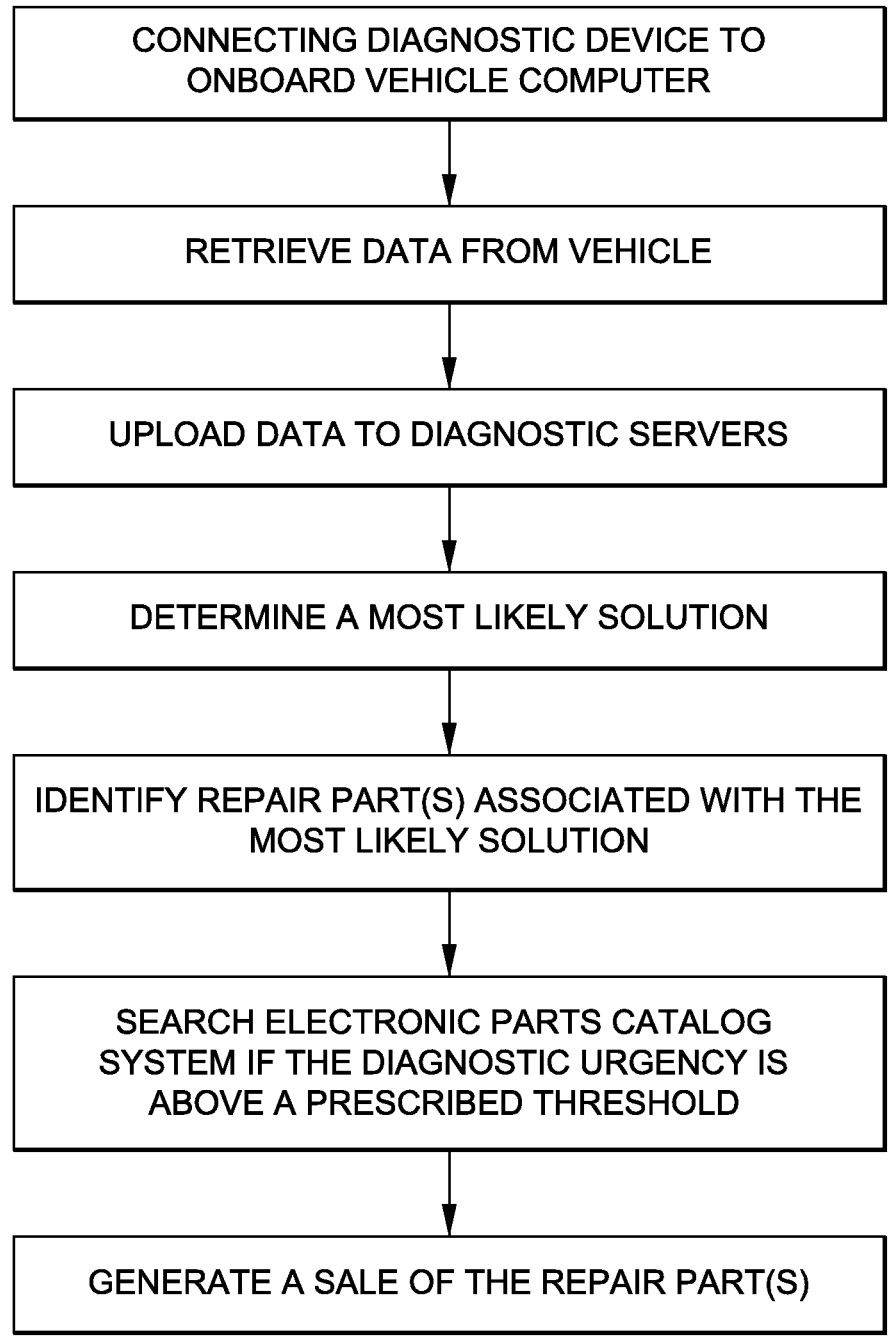
FIG. 7 is a flow chart illustrating an e-commerce application of the present invention.

While the previous discussion is largely directed toward the communication of information between the vehicle 1 and a remote location, the following discussion is focused on the use of that information once it is received at the remote location. In particular, the information may be used as part of one or more e-commerce applications. For instance, once the diagnostic information is received by a diagnostic database 24, the information may be analyzed to determine a most likely solution, and to identify a repair part associated with that diagnostic solution. The system may be linked with one or more parts stores and repair shops Referring now to FIG. 7, there is shown a method of generating a business transaction based on information retrieved from a vehicle. The method includes connecting the diagnostic device to the onboard vehicle computer to retrieve data and information therefrom. The data may include diagnostic data, such as DTCs, freeze frame data, and other data commonly retrieved from the onboard computer, in addition to vehicle identification information. Such vehicle identification information may include the vehicle identification number (VIN) or alternatively the year, make, model, and engine type of the vehicle. The diagnostic data and vehicle information retrieved from the onboard computer is uploaded to a communications network. As described in more detail above, the uploading of diagnostic data and vehicle information may be facilitated through the use of an intermediate wireless communication device, such as a smart phone, tablet computer, scan tool adapter, wireless router, or other hand transportable intermediate communication devices adapted for RF communication known, or later developed, by those skilled in the art. Furthermore, the communication network 110 may include the Internet, a telephone communication network, a local area network, or other RF communication networks known in the art.

The diagnostic data may be communicated to a solution database 24 from the communication network 110. The solution database 24 is configured to match the diagnostic data with stored solutions to identify a most likely solution that is associated with the uploaded diagnostic data. In some cases, the most likely solution may be as simple as ensuring that the gas cap is properly secured to the vehicle. In other cases, the most likely solution will require a repair part. For instance, the most likely solution may be that a mass airflow sensor needs to be replaced.

When the most likely solution involves a repair part, the most likely solution is communicated to a repair parts identification database 112. The repair parts identification database 112 includes repair parts organized according to vehicle identification information and matched with a universal part identification number. Each universal part identification number is also matched with an urgency status. An example of a universal parts identification system is the Aftermarket Catalog Enhanced Standard (ACES) parts numbering system, although other universally accepted parts identification systems may also be used in connection with the present invention without departing from the spirit and scope of the present invention.

The repair part identified by the most likely solution may be matched with the parts listed in the repair parts identification database to determine the universal part number associated with the repair part. However, it is understood that a given part (e.g., a mass airflow sensor) may vary from one vehicle to the next. Accordingly, there may be several universal part identification numbers associated with the different mass airflow sensors. As such, in order to identify a specific mass airflow sensor that is adapted for use with a specific vehicle, vehicle identification information is required. As such, the repair parts identification database 112 may receive that vehicle identification information as part of the upload from the diagnostic device.

It is also contemplated that in addition to parts being assigned universal identification numbers, vehicles may also be assigned a universal vehicle identification number, which corresponds to vehicles having the same year, make, model, and engine type. Thus, once a vehicle has been identified, the specific parts used on that vehicle may also be identified. Consequently, each universal vehicle identification number will be associated with various universal part identification numbers. When the vehicle under consideration has been identified, the universal part numbers associated with the vehicle may be focused on to simplify the analysis. Therefore, the searching for the diagnostic urgency may be simplified once the universal vehicle identification number is known because it will define a limited number of universal part identification numbers which can be searched.

When the system determines that a repair is needed, the system may take steps to quickly effectuate the repair. One particular aspect of the system is that certain steps in the overall process may proceed automatically, without any input from the user, thereby reducing the burden on the user.

According to one embodiment, diagnostic data (e.g., DTCs) may be automatically uploaded from the device 6 to a diagnostic database, such as the solution database 24. The upload of diagnostic data may be completed through the use of an intermediate device, such as a cellphone, or the device 6 may include onboard hardware capable of uploading the information directly. The data may be uploaded in response to a command entered by the user (e.g., the user actuating a button on the device 6 or a linked device, such as a smartphone), or in response to a predefined triggering condition. According to one embodiment, the diagnostic device may automatically upload diagnostic data to the intermediate wireless communication device when the diagnostic device moves into an area associated with the intermediate wireless communication device. The area associated with the intermediate wireless communication device (e.g., a wireless router) may be of a radius equal to 10-100 yards, although the size of the area associated with the intermediate wireless communication device will be dependent upon the size and strength thereof, and thus, it is understood that the area may be of a radius less than 10 yards or greater than 100 yards without departing from the spirit and scope of the present invention. For instance, the device 6 may be associated with a particular parts store 150 such that when the vehicle 12 (having the device 6 plugged into the vehicle 12) enters a predefined area around the parts store 150, such as the parking lot, the device 6 automatically uploads the information to the diagnostic databases 212 associated with the parts store 150. The upload of information may be effectuated by a wireless router or WiFi network associated with the parts store 150. The triggering condition is not limited to the device 6 moving into a predefined area around the parts store 150. Rather, the predefined triggering condition may also include one of the following: the device 6 being in wireless communication with a predefined wireless network (e.g., public or private Internet access), the device 6 moving into a predefined area around a service garage, the device 6 returning home or to a garage, the engine being turned ON, the engine being turned OFF, a DTC being generated by the vehicle. Of course, those skilled in the art will appreciate that the aforementioned triggering conditions are exemplary in nature only, and are not intended to limit the scope of the present invention. Along these lines, other triggering conditions known in the art may also be used without departing from the spirit and scope of the present invention.

Once the information from the vehicle 12 is uploaded to the diagnostic databases 212, a most likely solution is determined, along with a corresponding repair part. As with the upload of diagnostic information to the database 212, the analysis of the diagnostic information at the database 212 may be completed automatically without input from the user.

When the diagnostic conclusion results in a most likely solution associated with a repair part, the system may automatically complete the sale of the repair part to expedite the repair. In other embodiments, the system may prompt the user to ask the user whether completion of the sale is desired. This prompt may be displayed on the user's smartphone via text message, email or other forms of electronic communication.

The process of completing the sale of the repair part may be controlled by a purchasing module, which may establish a link between the diagnostic database 212 and an electronically searchable parts catalog or database 115 (e.g., an inventory database) to determine if the parts store 150 carries the specific repair part needed (e.g., the repair part associated with the specific part number), if the repair part is in stock, as well as determining the price of the repair part. The search of the parts database 115 may be completed automatically without any input from the user. It is contemplated that a plurality of parts databases 115 associated with different parts stores may be searched to find the nearest repair part and/or the least expensive repair part.

The system may be configured to automatically ship the part to the user to allow the user to complete the repair. Alternatively, the part may be set aside for the user at the parts store for pickup. In other embodiments, the sale of the part may not be completed until the user arrives at the store. The user may be sent part tracking information to enable quick and easy completion of the sale once the user arrives at the store. For instance, the system may send an email and/or text message to the user with a reference number, tracking number, bar code, or other transaction identification information to simplify the sale when the user arrives at the store. The part information may also be displayed for the customer at the parts store to allow the customer to visually confirm the information prior to purchase.

In addition to automatically generating a sale of the part, the system may also automatically schedule a repair to install the new repair part. The automatic scheduling of the repair may be particularly useful in fleet management applications. When a repair is automatically scheduled, the user/fleet manager may be sent a message with details associated with the repair, such as the date/time of the repair, estimate time to complete the repair, cost of the parts/service, etc.

The above description is given by way of example, and not limitation. Given the above disclosure, one skilled in the art could devise variations that are also within the scope and spirit of the invention disclosed herein, including various ways of linking a vehicle diagnostic port to a local connectivity circuit to access a cellular telephone network, and beyond. Further, the various features of the embodiments disclosed herein can be used alone, or in varying combinations with each other and are not intended to be limited to the specific combination described herein. Thus, the scope of the claims is not to be limited by the illustrated embodiments or interpretation of those embodiments.

What is claimed is:

1. A vehicular diagnostic system for use with a vehicle associated with vehicle identification information, the vehicular diagnostic system comprising:
 a) a hand transportable diagnostic device having:
  1) a vehicle diagnostic port connector for receiving vehicle diagnostic data from a vehicle diagnostic port located on the vehicle; and
  2) a local wireless radio frequency (RF) communication circuit, in communication with the vehicle diagnostic port, for communicating vehicle diagnostic data between the vehicle diagnostic port connector and a local wireless RF communication network;
 b) an intermediate, hand transportable wireless RF communication device in communication with the local wireless communication network for receiving vehicle diagnostic data from the diagnostic device, the intermediate wireless communication device being separate from the diagnostic device;
 c) a diagnostic database in wireless RF communication with the intermediate wireless communication device, the diagnostic database being configured to automatically derive vehicle identification information from the diagnostic data, to automatically match the vehicle identification information and diagnostic data from the vehicle with a most likely diagnostic solution, and to automatically identify at least one repair part associated with the most likely solution, in response to receipt of the diagnostic data at the diagnostic database; and
 d) a repair parts database in communication with the diagnostic database, the repair parts database having information associated with a plurality of repair parts, each repair part being associated with specific vehicle identification information and a specific universal part number, the repair parts database being configured to automatically identify the specific universal part number in response to receipt of the identified repair part(s) and the vehicle identification information at the repair parts database;

e) wherein the diagnostic device includes an autonomous data transfer circuit that automatically initiates communication of diagnostic data to the intermediate wireless communication device in response to receipt of the vehicle diagnostic data at the diagnostic device diagnostic port connector;

wherein the wireless communication device is operative to regulate communication of diagnostic data between the diagnostic device and the diagnostic database.

2. The system recited in claim 1, wherein the universal part identification number is an Aftermarket Catalog Enhanced Standard (ACES) part number.

3. The system recited in claim 1, wherein the diagnostic device is adapted to receive the vehicle identification information from the vehicle through the vehicle diagnostic port connector.

4. The system recited in claim 1, further comprising an inventory database in communication with the repair parts database, the inventory database being configured to automatically search for an inventoried part associated with the universal part identification number in response to receipt of the universal part identification number from the parts database.

5. The system recited in claim 4, further comprising a purchasing module in communication with the inventory database, the purchasing module being configured to automatically conduct a transaction for the purchase of the inventoried part associated with the universal parts identification number.

6. The system recited in claim 1, wherein the intermediate wireless communication device is a cellphone.

7. The system recited in claim 1, wherein the intermediate wireless communication device is a wireless router.

8. The system recited in claim 1, wherein the diagnostic device automatically uploads diagnostic data to the intermediate wireless communication device when the diagnostic device moves into an area associated with the intermediate wireless communication device.

9. The system recited in claim 8, wherein the area associated with the intermediate wireless communication device is 10-100 yards from the wireless communication device.

10. The system as recited in claim 1 wherein the wireless communication device is operative to generate an indication signal upon receipt of diagnostic data from the diagnostic device.

11. The system as recited in claim 10 wherein the wireless communication device is operative to automatically communicate the diagnostic data to the diagnostic database in response to receipt of the diagnostic data from the diagnostic device.

12. The system as recited in claim 1 wherein the wireless communication device is operative to automatically communicate the diagnostic data to the diagnostic database in response to a user input command generated on the wireless communication device.

13. The system as recited in claim 1 wherein the wireless communication device is operative to automatically generate an indication signal in response to receipt of one or more predetermined trouble codes from the diagnostic device.

14. The system as recited in claim 13 wherein the wireless communication device is further operative to initiate a communications link with the diagnostic device.

15. A method of diagnosing a vehicle having vehicle identification information, the method comprising the steps of:

a) retrieving vehicle diagnostic data from the vehicle using a hand transportable diagnostic device connected to a vehicle diagnostic port;

b) initiating communication of vehicle diagnostic data to a remote diagnostic database in response to receipt of the vehicle diagnostic data by the diagnostic device;

c) wirelessly communicating the vehicle diagnostic data by radio frequency (RF) transmission from the diagnostic device to a separate, intermediate hand transportable wireless RF communication device;

d) wirelessly communicating the vehicle diagnostic date by RF transmission from the intermediate hand transportable wireless communication device to a remote diagnostic database;

e) deriving vehicle identification information from the vehicle diagnostic data at the diagnostic database;

f) analyzing the vehicle diagnostic data at the diagnostic database to match the diagnostic data from the vehicle with a most likely solution associated with at least one repair part; and g) analyzing the repair part at a repair parts database to identify a specific universal part number associated with the repair part, the repair parts database having information associated with a plurality of repair parts, each repair part being associated with specific vehicle identification information and a specific universal part number that the repair parts database identifies when the repair part and vehicle identification information are known;

h) wherein the steps of e), f) and g) proceed automatically in response to receipt of the diagnostic data at the diagnostic data database.

16. The method recited in claim 15, wherein the vehicle diagnostic data is automatically communicated from the diagnostic device to the intermediate wireless communication device when the diagnostic device enters an area associated with the intermediate wireless communication device.

17. The method recited in claim 15, wherein the intermediate wireless communication device is a cellphone.

18. The method recited in claim 15, wherein the intermediate wireless communication device is a wireless router.

19. The method recited in claim 15, wherein the universal part identification number is an Aftermarket Catalog Enhanced Standard (ACES) part number.

20. The method recited in claim 15, further comprising the step of searching an inventory database for an inventoried part associated with the universal part identification number.

21. The method recited in claim 15, wherein the communicating step is performed autonomously, independent of any user input.

22. The method as recited in claim 15 further including the step of generating an indication signal at the wireless communication device, in response to receipt of diagnostic data from the diagnostic device.

23. The method as recited in claim 15 further including the step of automatically initiating an RF communication link with the diagnostic database at the wireless communication device, in response to receipt diagnostic data from the diagnostic device.

24. The method as recited in claim 23 further including the step of automatically initiating an RF communications link with the diagnostic database at the wireless communication device, in response to a user input command generated on the wireless communication device.

25. The method as recited in claim 15 further including the step of generating an indication signal, at the wireless communication device, in response to receipt of one or more predetermined trouble codes from the diagnostic device.

26. The method as recited in claim 25 further including the step of initiating an RF communications link with the diagnostic device, at the wireless communication device.

27. The method as recited in claim 15 further including the step of initiating an RF communication link between the wireless communication device and the diagnostic database in response to a user input command generated on the wireless communication device.

28. The method as recited in claim 15 wherein steps b) thru f) proceed automatically in response to turning on the vehicle.

29. The method as recited in claim 15 wherein steps b) thru f) proceed automatically in response to turning off the vehicle.

30. The method as recited in claim 15 wherein steps b) thru f) proceed automatically in response to the vehicle entering a service area associated with the wireless communication device.

31. The method as recited in claim 15 further comprising the steps of:
  i) determining if the repair part identified by the universal part number is in stock; and
  j) determining the price of the repair part associated with the universal part number;
  wherein steps of c) thru j) proceed automatically in response to receipt of the vehicle diagnostic data at the diagnostic database, without input from a user.

32. The method as recited in claim 31 further including the step of:
  k) scheduling a repair to install the repair part associated with the universal identification number; and
  l) determining the cost of parts and services to complete the repair;
  wherein steps of c) thru l) proceed automatically in response to receipt of the vehicle diagnostic data at the diagnostic database, without input from the user.

33. A vehicular diagnostic system for use with a vehicle associated with vehicle identification information, the vehicular diagnostic system comprising:
  a) a hand transportable diagnostic device having:
    1) a vehicle diagnostic port connector for receiving vehicle diagnostic data from a vehicle diagnostic port located on the vehicle; and
    2) a local wireless radio frequency (RF) communication circuit, in communication with the vehicle diagnostic port, for communicating vehicle diagnostic data between the vehicle diagnostic port connector and a local wireless RF communication network;
  b) an intermediate, hand transportable wireless RF communication device in communication with the local wireless communication network for receiving vehicle diagnostic data from the diagnostic device, the intermediate wireless communication device being separate from the diagnostic device;
  c) a diagnostic database in wireless RF communication with the intermediate wireless communication device, the diagnostic database being configured to automatically derive vehicle identification information from the diagnostic data, to automatically match the vehicle identification information and diagnostic data from the vehicle with a most likely diagnostic solution, and to automatically identify at least one repair part associated with the most likely solution, in response to receipt of the diagnostic data at the diagnostic database; and
  d) a repair parts database in communication with the diagnostic database, the repair parts database having information associated with a plurality of repair parts, each repair part being associated with specific vehicle identification information and a specific universal part number, the repair parts database being configured to automatically identify the specific universal part number in response to receipt of the identified repair part(s) and the vehicle identification information at the repair parts database;
  e) wherein the diagnostic device includes an autonomous data transfer circuit that automatically initiates communication of diagnostic data to the intermediate wireless communication device in response to receipt of the vehicle diagnostic data at the diagnostic device diagnostic port connector.

34. The system recited in claim 33, wherein the universal part identification number is an Aftermarket Catalog Enhanced Standard (ACES) part number.

35. The system recited in claim 33, wherein the diagnostic device is adapted to receive the vehicle identification information from the vehicle through the vehicle diagnostic port connector.

36. The system recited in claim 33, further comprising an inventory database in communication with the repair parts database, the inventory database being configured to automatically search for an inventoried part associated with the universal part identification number in response to receipt of the universal part identification number from the parts database.

37. The system recited in claim 33, further comprising a purchasing module in communication with the inventory database, the purchasing module being configured to automatically conduct a transaction for the purchase of the inventoried part associated with the universal parts identification number.

38. The system recited in claim 33, wherein the intermediate wireless communication device is a cellphone.

39. The system recited in claim 33, wherein the intermediate wireless communication device is a wireless router.

40. The system recited in claim 33, wherein the diagnostic device automatically uploads diagnostic data to the intermediate wireless communication device when the diagnostic device moves into an area associated with the intermediate wireless communication device.

41. The system recited in claim 33, wherein the area associated with the intermediate wireless communication device is 10-100 yards from the wireless communication device.

42. The system as recited in claim 33 wherein the wireless communication device is operative to automatically generate an indication signal upon receipt of diagnostic data from the diagnostic device.

43. The system as recited in claim 33 wherein the wireless communication device is operative to automatically communicate the diagnostic data to the diagnostic database in response to receipt of the diagnostic data from the diagnostic device.

44. The system as recited in claim 33 wherein the wireless communication device is operative to automatically communicate the diagnostic data to the diagnostic database in response to a user input command generated on the wireless communication device.

45. The system as recited in claim 33 wherein the wireless communication device is operative to automatically generate an indication signal in response to receipt of one or more predetermined trouble codes from the diagnostic device.

46. The system as recited in claim 33 wherein the wireless communication device is further operative to initiate a communications link with the diagnostic device.

\* \* \* \* \*